(12) United States Patent
Baltschun et al.

(10) Patent No.: US 6,425,896 B1
(45) Date of Patent: Jul. 30, 2002

(54) ENDOSCOPICALLY USEABLE INSTRUMENT FOR COAGULATION BY MEANS OF HIGH FREQUENCY AND FOR THE SERVING OF COAGULATED TISSUE AREAS

(75) Inventors: Horst Baltschun, Rulzheim; Klaus-Peter Brhel, Philippsburg; Bernhard Kneifel, Hagenbach, all of (DE)

(73) Assignee: Forschungszentrum Karlsruhe GmbH, Karlsruhe (DE)

( * ) Notice: Subject to any disclaimer, the term of this patent is extended or adjusted under 35 U.S.C. 154(b) by 0 days.

(21) Appl. No.: 09/592,541

(22) Filed: Jun. 12, 2000

(30) Foreign Application Priority Data

Jul. 28, 1999 (DE) .......................................... 199 35 478

(51) Int. Cl.$^7$ .............................................. A61B 18/14
(52) U.S. Cl. .............................. 606/51; 606/46; 606/52; 606/170; 606/174
(58) Field of Search ........................ 606/45, 46, 48–52, 606/170, 174, 205–208

(56) References Cited

U.S. PATENT DOCUMENTS

| | | | | |
|---|---|---|---|---|
| 4,655,216 A | * | 4/1987 | Tischer | 606/51 |
| 5,445,638 A | * | 8/1995 | Rydell et al. | 606/51 |
| 5,797,941 A | * | 8/1998 | Schulze et al. | 606/51 |
| 5,908,420 A | * | 6/1999 | Parins et al. | 606/51 |
| 5,964,758 A | * | 10/1999 | Dresden | 606/45 |

* cited by examiner

Primary Examiner—Lee Cohen
(74) Attorney, Agent, or Firm—Klaus J. Bach

(57) ABSTRACT

In an endoscopic surgical instrument for the coagulation, by high frequency energy, and for the severing of coagulated tissue areas, a coagulation pliers and a scissors structure are provided, which are mounted on the distal end of an instrument and which are operated by a handle with operating levers in such a way that, upon actuation of the handle, first the pliers is closed for grasping the tissue while the scissors are closed in a delayed fashion. After coagulation of the tissue engaged by the pliers, actuation of a second lever at the handle end of the instrument fully closes the scissors structure for cutting the tissue in the coagulation area.

5 Claims, 2 Drawing Sheets

ENDOSCOPICALLY USEABLE INSTRUMENT FOR COAGULATION BY MEANS OF HIGH FREQUENCY AND FOR THE SERVING OF COAGULATED TISSUE AREAS

BACKGROUND OF THE INVENTION

The invention resides in an endoscopically useable surgical instrument for the coagulation of tissue by high frequency application and for the severing of coagulated tissue areas.

Such an instrument is disclosed in German patent P44 21 822 C1. The instrument shown therein has a stationary and a movable jaw with two ranges of movement. The contact surfaces of the two jaws move apart during opening of the jaws first in a parallel fashion. Subsequently, the movable jaw can be pivoted about a pivot axis up to its maximum opening position. With one hand operating the handle, the coagulation apparatus with integrated cutting structure can perform first the coagulation and subsequently, the cutting process by way of a lever mechanism.

It is however a disadvantage of this design that the movable jaw is supported and guided in an unstable manner because of the initial parallel opening movement followed by the pivoting movement: When the clamping forces become large, the movable jaw is canted, whereby the force grasping the tissue is reduced. The subsequent cutting step is performed by an axi ally movable cutting blade, which pushes the tissue to be cut forwardly out of the blade when the cutting resistance becomes excessive or the clamping force is too small.

The printed publication EP 0 572 131 A1 discloses a pair of surgical scissors with a bipolar coagulation arrangement including a stationary and a pivotable cutting blade which is operable by a handle by way of an operating rod. This instrument is also designed for minimally invasive surgery.

With the bipolar surgical scissors, the coagulation and severing of the tissue is performed by the cutting edges of the scissors. In this case, however, it cannot be made sure whether the severed tissue is fully coagulated so that bleeding may well occur during cutting.

It is the object of the present invention to provide a bipolar HF coagulation apparatus with an integrated cutting structure and a handle portion for the operation of the apparatus with one hand whereby the cutting performance is improved and which can be used in minimally invasive surgery.

SUMMARY OF THE INVENTION

In an endoscopic surgical instrument for the coagulation, by high frequency energy, and for the severing of coagulated tissue areas, a coagulation pliers and a scissors structure are provided, which are mounted on the distal end of an instrument and which are operated by a handle with operating levers in such a way that, upon actuation of the handle, first the pliers is closed for grasping the tissue while the scissors are closed in a delayed fashion. After coagulation of the tissue engaged by the pliers, actuation of a second lever at the handle end of the instrument fully closes the scissors structure for cutting the tissue in the coagulation area.

The pivot movement of the lever is transmitted to inner tubes of the tubular instrument as longitudinal movement. The longitudinal movement is then converted to pivot movement of the pliers and scissors by way of cross-levers.

The sub-claims define various advantageous embodiments of the invention.

It is essential that, during the closing movement, the scissors movement follow the movement of the coagulation pliers with a predetermined delay. This movement is controlled by the lever arm ratios of the cross levers. The cutting step to be performed after coagulation is completed by a second cross-lever. The invention will be described in greater detail on the basis of the accompanying drawings.

DESCRIPTION OF A PREFERRED EMBODIMENT

Figure 1:
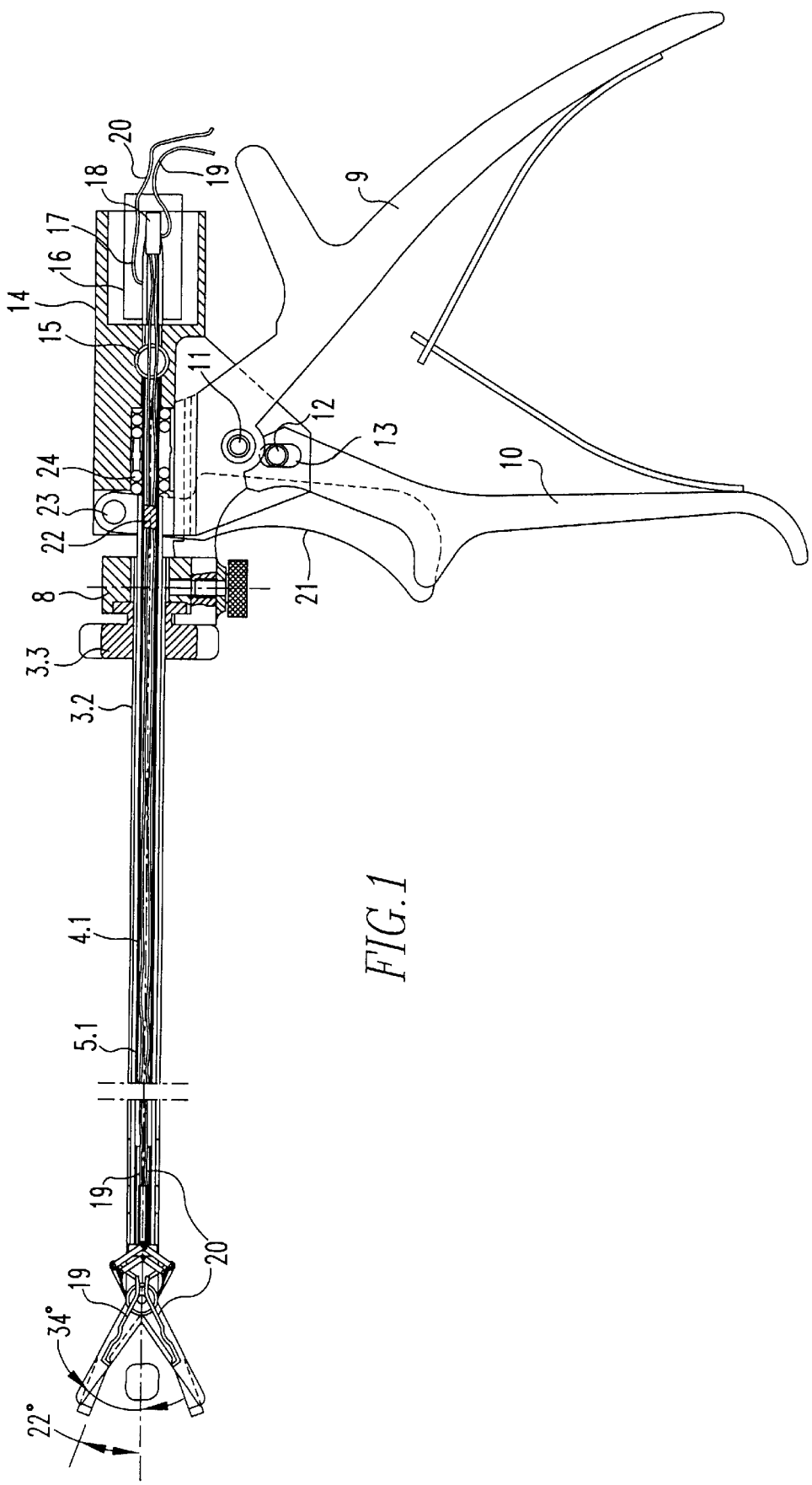
FIG. 1 is a side elevational view of the coagulation apparatus in accordance with the present invention.

FIG. 1 shows the preferred embodiment of the coagulation apparatus wherein the coagulation pliers 1 and the scissors 2 are separately operable, each by a pivotable handle portion 10 and 21. Two subsequent closing movements provide for the coagulation procedure and the subsequent severing of the tissue.

First, the tissue is compressed by the pliers 1, 1' with the pivotable handle 10. The tissue is then coagulated in the area of the surfaces 1.2 and 1.2' by switching on the high frequency. Subsequently, the scissors 2 are operated by the handle 21, whereby the coagulated tissue is severed.

FIG. 1 shows the pliers 1 and the scissors 2 in the initial position with maximum opening angle. They are held in this basic position by the spring-biased pivot handles 10, 21. The parts 1 and 1' of the pliers are of the same design and arranged mirror-reversed. They include longitudinal center grooves 1.1, 1.1' in their sides toward their longitudinal centers for receiving the scissors 2. At their pivot points, the pliers parts 1 and 1' are pivotally supported on the fork head 3 by way of the shaft 1.4.

At the front-end area of the pliers part 1, there is the coagulation surface area 1.2, extending in a plane parallel to the shaft 1.4. Insulation layers 1.3, 1.2' separate the coagulation areas 1.2 from the pliers parts 1, 1'. At the rear end of the pliers part 1, there is a bore 1.5 for the connection of the strap 6 forming part of a cross-lever structure 6, 6'. The pliers parts 1, 1' are connected by the cross-lever structure 6, 6' to a head portion 5, which is attached to the front end of a first inner tube 5.1. At the other end of the inner tube 5.1 there are the contact areas 17 and 18 for the connection of high frequency power supply lines 19 and 20. The inner tube 5.1, further is provided with a coupling member 15, which interconnects the tube 5.1 and a slide member 14.

The outer parts of the coagulation apparatus start at the front of the apparatus with the fork structure 3. The fork structure 3 includes a stepped area 3.1 to which the tube 3.2 is mounted with one end thereof, while it is connected, at its other end, to the rotational member 3.3. The rotational member 3.3 is rotatably supported on the coupling member 8, which again is connected to the handle 9 in a stationary fashion. With the rotational member 3.3, the distal end of the coagulation apparatus with the pliers 1 and the scissors 2 can be rotated about the axis of the tube 3.2.

The movable handle 10 is supported on the stationary handle 9 so as to be pivotable about the shaft 11. Below the shaft 11, the pivotable handle 10 includes a bolt 12, which is received in an elongated opening 13 formed in a slide member 14. Pivot movement of the handle 10 is transferred by way of the bolt 12 and the elongated opening 13 as an axial movement to the slide member 14 and to the coupling member 15. The coupling member 15 is connected to the inner tube 5.1 at the other end of which the headpiece 5 is disposed. The straps 6, 6' couple the headpiece 5 to the pliers parts 1, 1'. In this way, the longitudinal movement of the inner tube 5.1 is converted to a pivot movement of the pliers 1, 1'. With the axial movement of the slide member 14, the handle 21, the coupling bolt 22 with the inner tube 4.1 and the headpiece 4 are displaced by the same distance. The straps 7,7' interconnect the headpiece 4 and the scissors 2 and convert the longitudinal movement of the tube 4.1 into a pivot movement of the scissor arms 2, 2'. Since the distance of the scissors pivot axis to the scissors operating connection 2.1 is greater than the distance between the pliers pivot point 1.4 and the pliers operating connection 1.5, the pliers 1 will move by a greater pivot angle than the scissors 2, with the same axial movement of the inner tubes. This difference is apparent in the representation of FIG. 1 (base position) with respect to FIG. 2 (coagulation position) and has the purpose that the scissor arms 21 are maintained at a greater distance from the coagulation surface area 1.2 than the pliers in order to avoid injuries to the tissue by the cutting edges of the scissors. Two insulated cables 19, 20 conduct the high frequency from the contacts 17, 18 in the inner tube 5.1 to the head piece 5 and from there to the coagulation surface area 1.2 of the pliers 1. The HF power is switched on by a switch, preferably a foot-operated switch, which is not shown.

Figure 2:
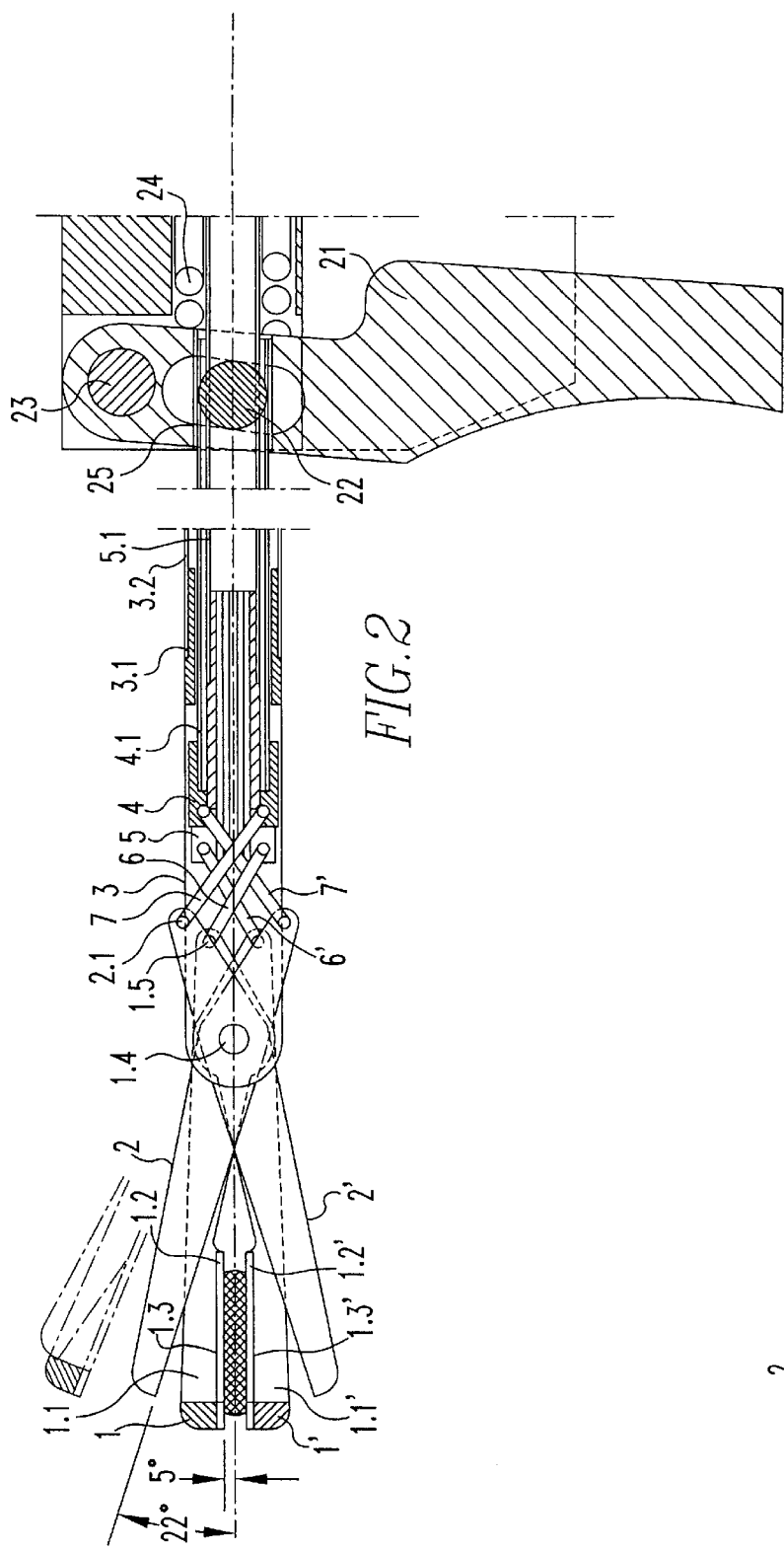
FIG. 2 is a side elevational view of the instrument in operating position.

FIG. 2 shows the operating position for the coagulation procedure. The high frequency for the bipolar coagulation is supplied, by a two-pole coupling member 16, to the contact locations 17 and 18, which are arranged at the end of the inner tube 5.1. The pivot movement of the pliers 1 and the scissors 2 is obtained by the closing movement of the lever 10 as shown in FIG. 2 because the compression spring 24, which is supported with one end on the slide member 14, presses with the other end against the lever 21 with the coupling bolt 22, the tube 4.1 and the headpiece 4 and against the head piece 5. With the closing movement of the lever 10, the two headpieces 4 and 5 are therefore moved axially and their movement is transferred to the pliers 1 and the scissors 2 by way of the straps 6 and 7.

Figure 3:
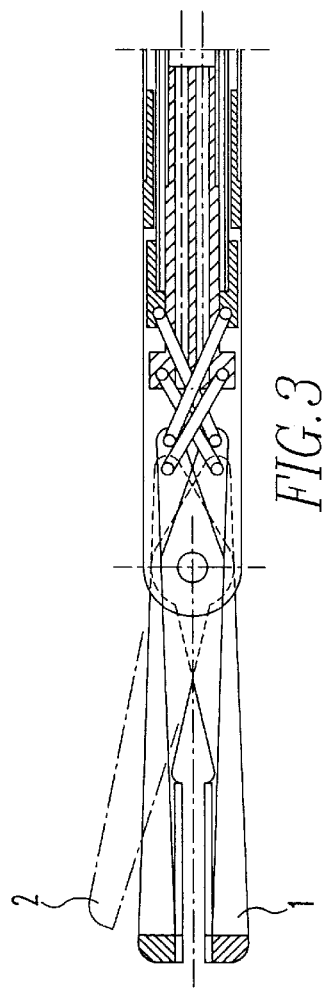
FIG. 3 is an elevational view of the instrument in cutting position.

FIG. 3 shows the distal end of the instrument with the pliers 1 and the scissors 2 in the operating position "cutting". The final cutting movement of the scissors 2 is achieved by operating the lever 21. The lever 21 is pivotally supported on the slide member 14 by a bolt 23. The lever 21 is connected to the tube 4.1 and the headpiece 4 by a coupling bolt 22. With the operation of the lever 21, the headpiece 4 is moved away from the pivot point 1.4 of the scissors 2. The movement of the headpiece 4 is transferred to the scissors 2 by way of the straps 7, 7' and is converted to a pivot—that is, a final closing movement of the scissors.

What is claimed is:

1. An endoscopic surgical combination instrument for the high frequency coagulation and the subsequent severing of tissue areas, comprising: an outer tube including a handle portion at a proximal end thereof and, at a distal end thereof, a coagulation pliers with two coagulation surface areas disposed on arms which are movable toward, and away from, each other, said arms being supported so as to be pivotable about a pivot axis and one of said coagulation surface areas being disposed at the free end of each arm, a pair of scissors having arms with cutting edges pivotally supported so as to be movable relative to each other in a mirror-like fashion, a drive structure for said coagulation pliers comprising a longitudinally movable first inner tube disposed in said outer tube and having a distal end with a first head and a cross-lever structure including straps connecting said first head with said coagulation pliers for operating said coagulation pliers by longitudinal movement of said first inner tube, a drive structure for said pair of scissors comprising a longitudinally movable second inner tube having a distal end with a second head and a cross lever structure including straps connecting said second head with said scissors arms for operating said scissors, an operating part disposed on said handle portion at the proximal end of said outer tube including a handle and a pivot lever for operating said coagulation pliers and said pair of scissors against the force of a handle spring disposed between said handle and said pivot lever for returning said pivot lever after said pivot lever has been pulled toward said handle, a second lever mounted on said handle and engaging said second inner tube for operating said scissors and a coil spring disposed in said handle portion and engaging said second lever for returning said second lever after it has been actuated by an operator, whereby said coagulation pliers and said scissors are normally held in a fully open position, but, by pulling said pivot lever toward said handle, said first inner tube is pulled toward said proximal end and said first head engages said second head which then follows the backward movement of said first head such that, first, said coagulation pliers is closed followed by a partial closing of said scissors as determined by the lever ratios of said cross lever structures, and subsequently, upon pulling of said second lever toward said handle, the second inner tube is further retracted and said scissors are closed for cutting the tissue area engaged by said pliers which area has coagulated in the meantime by application of high frequency and said scissors and said coagulation pliers are again opened upon release of said second and said pivot levers resulting in the forward movement of the two inner tubes.

2. An instrument according to claim 1, wherein said two coagulation surface areas are disposed on the respective arms of the pliers by means of an insulation layer.

3. An instrument according to claim 2, wherein the cutting edges of said scissors are removably mounted on said scissors arms.

4. An instrument according to claim 2, wherein said coagulation pliers includes areas which are covered by a tissue-compatible dielectric layer in order to prevent high frequency leakage currents from reaching the surrounding tissue.

5. An instrument according to claim 4, wherein a rotatable member is supported at the end of said outer tube remote from said handle structure, said rotatable member facilitating rotation of the distal end of said outer tube with the pliers and together therewith of said scissors relative to said handle.

* * * * *